United States Patent
Behar-Cohen et al.

(10) Patent No.: US 9,192,512 B2
(45) Date of Patent: Nov. 24, 2015

(54) DEVICE FOR DELIVERING MEDICINES BY TRANSPALPEBRAL ELECTROPHORESIS

(71) Applicant: Eyegate Pharma S.A.S., Paris (FR)

(72) Inventors: Francine Behar-Cohen, Paris (FR); Pierre Roy, Paris (FR)

(73) Assignee: EYEGATE PHARMA S.A.S., Paris (FR)

( * ) Notice: Subject to any disclaimer, the term of this patent is extended or adjusted under 35 U.S.C. 154(b) by 0 days.

(21) Appl. No.: 14/286,544

(22) Filed: May 23, 2014

(65) Prior Publication Data

US 2014/0323947 A1 Oct. 30, 2014

Related U.S. Application Data

(60) Division of application No. 12/913,065, filed on Oct. 27, 2010, now Pat. No. 8,771,256, which is a continuation of application No. 10/492,494, filed as application No. PCT/FR02/03472 on Oct. 11, 2002, now Pat. No. 7,848,800.

(30) Foreign Application Priority Data

Oct. 12, 2001 (FR) .................................... 01 13176

(51) Int. Cl.
*A61N 1/30* (2006.01)
*A61F 9/00* (2006.01)
*A61N 1/32* (2006.01)
*A61N 1/04* (2006.01)

(52) U.S. Cl.
CPC .............. *A61F 9/0017* (2013.01); *A61N 1/044* (2013.01); *A61N 1/0436* (2013.01); *A61N 1/0448* (2013.01); *A61N 1/325* (2013.01); *A61N 1/0412* (2013.01)

(58) Field of Classification Search
CPC ... A61N 1/044; A61N 1/0412; A61N 1/0436; A61N 1/0448; A61N 1/325; A61N 9/0017; A61N 1/30; A61N 1/303; A61N 1/0428; A61N 1/0492; A61N 1/0472; A61N 9/0008; A61N 1/0543; A61M 2210/0612
USPC .......................................................... 604/20
See application file for complete search history.

(56) References Cited

U.S. PATENT DOCUMENTS

| | | |
|---|---|---|
| 3,845,757 A | 11/1974 | Weyer |
| 4,564,016 A | 1/1986 | Maurice et al. |
| 4,603,076 A | 7/1986 | Bowditch |
| 5,169,384 A | 12/1992 | Bosniak et al. |

(Continued)

FOREIGN PATENT DOCUMENTS

| | | |
|---|---|---|
| EP | 1127586 | 8/2001 |
| WO | 9940967 | 8/1999 |

OTHER PUBLICATIONS

International Search Report, Rokatondrajaona, C., Issued Mar. 26, 2003 for International Application No. PCT/FR02/03472.

*Primary Examiner* — Jason Flick

(74) *Attorney, Agent, or Firm* — Burns & Levinson LLP; Joseph M. Maraia

(57) ABSTRACT

The invention concerns a device for ocular application of an active principle (1) comprising a main electrode (2) including an insulating layer, an adhesive layer designed to bind the insulating layer to a conductive layer, characterized in that the main electrode comprises a zone (21, 22) designed to be urged into contact with an eyelid.

20 Claims, 3 Drawing Sheets

(56) References Cited

U.S. PATENT DOCUMENTS

Figure 1:
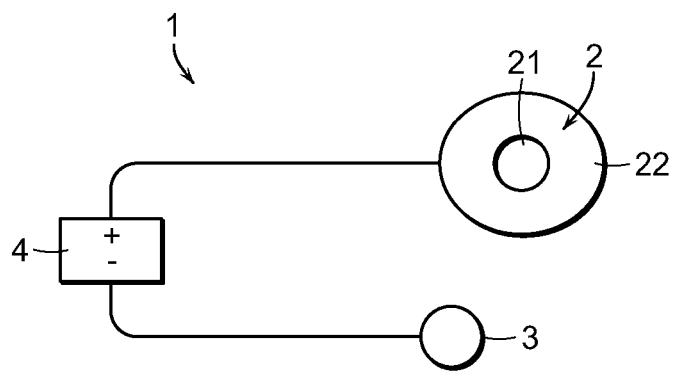

| | | |
|---|---|---|
| 5,320,597 A | 6/1994 | Sage, Jr. et al. |
| 5,356,632 A | 10/1994 | Gross et al. |
| 5,450,845 A | 9/1995 | Axelgaard |
| 5,520,180 A | 5/1996 | Uy et al. |
| 5,522,864 A | 6/1996 | Wallace et al. |
| 6,001,088 A | 12/1999 | Roberts et al. |
| 6,154,671 A | 11/2000 | Behar et al. |
| 6,277,401 B1 | 8/2001 | Bello et al. |
| 6,442,423 B1 | 8/2002 | Domb et al. |
| 6,477,410 B1 * | 11/2002 | Henley et al. .................. 604/20 |
| 6,503,231 B1 | 1/2003 | Prausnitz et al. |
| 6,546,284 B2 | 4/2003 | Plummer |
| 6,694,193 B2 | 2/2004 | Lyster et al. |
| 6,697,668 B2 | 2/2004 | Parkinson et al. |
| 2002/0099321 A1 | 7/2002 | Plummer |
| 2002/0099357 A1 | 7/2002 | Parkinson et al. |
| 2003/0023228 A1 | 1/2003 | Parkinson et al. |
| 2004/0106965 A1 | 6/2004 | Chow |

\* cited by examiner

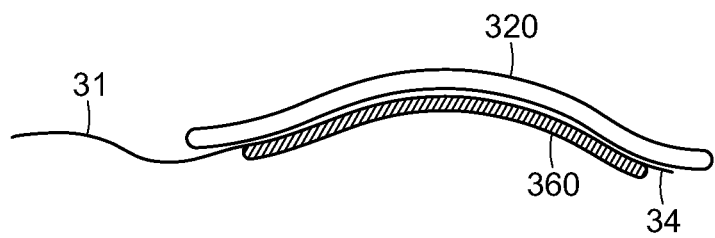
FIG. 4
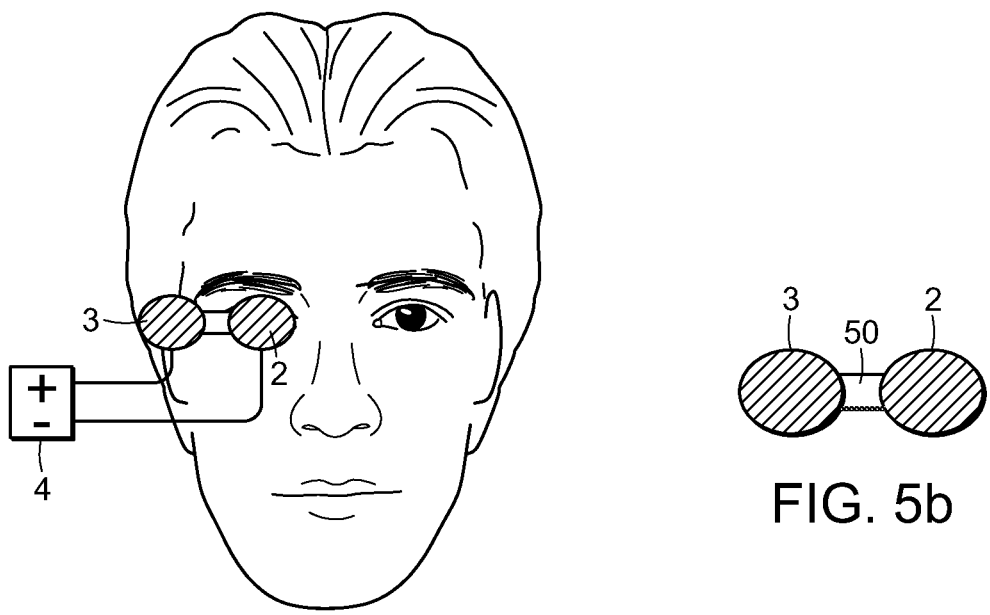
FIG. 5a
FIG. 5b

DEVICE FOR DELIVERING MEDICINES BY TRANSPALPEBRAL ELECTROPHORESIS

This application is a divisional of U.S. patent application Ser. No. 12/913,065 filed Oct. 27, 2010 entitled, "Device Delivering Medicines by Transpalpebral Electrophoresis", which is a continuation of U.S. Pat. No. 7,848,800 filed Apr. 9, 2004, entitled, "Device for Delivering Medicines by Transpalpebral Electrophoresis", which is the U.S. National Stage of International Application No. PCT/FR02/03472, filed Oct. 11, 2002, entitled, "Device for Delivering Medicines by Transpalpebral Electrophoresis," which claims priority to French Patent Application FR01/13176 filed Oct. 12, 2001, entitled, "Device for Delivering Medicines by Transpalpebral Electrophoresis" each of which are incorporated by reference in their entirety.

The invention concerns devices for delivering active substances in particular by transpalpebral iontophoresis.

Iontophoresis uses electric current to enable the diffusion of an ionised molecule through a biological membrane for therapeutic purposes. Under the effect of the electric current, the permeability of the biological membrane is increased, which allows the passage of larger molecules within the cell, and the electric field pushes the molecules through this membrane. This technique has the advantage compared with a conventional topical application of increasing the depth of penetration of the active substance in proportion to the current intensity used and the application time.

The present techniques for delivering active substances in the region of the eye can be classified into five categories described as follows:

the systemic route (oral route or intravenous route), sometimes by bolus (large dose, short duration) does not give high concentrations in the eye (less than 1%) since the blood vessels of the retina and other parts of the central nervous system are relatively impermeable to many active substances. Moreover, drugs used by the systemic route can have significant secondary effects on organs of the body other than the one explicitly targeted;

direct injections around the eye into the periocular spaces or the vitreous body are highly traumatising. Moreover, after injection into the vitreous body, the drug is quickly diluted and disappears in a few hours. This administration mode has certain risks such as risks of infection, bleeding, cataract or detachment of the retina. These problems can be partially solved by intra-ocular implants for programmed release of active substances implanted directly into the vitreous body, solid or semi-solid implants, sutured or not, which require a surgical operation to implant them and a second operation to withdraw those made of non-biodegradable materials;

topical applications by drops apply only to active products that can be formulated as a collyrium (solution or suspension) and cannot treat the posterior segment of the eyeball since penetration of the active substance is very limited and does not allow therapeutic concentrations to be achieved beyond the anterior segment of the eyeball. Furthermore, as tears wash away the drug quickly, the applications must be repeated frequently. It is possible to overcome these problems by using a conjunctival insert allowing a programmed release of active substances, whilst increasing the time of contact of the active substance with the ocular surface. This solution has the drawback of having a poor tolerance and a small benefit since it proves impossible to obtain high concentrations of active substance in the posterior segment of the eye (retina, optic nerve);

photodynamic therapy is a technique which consists of systemically injecting an active substance and activating it locally using a laser having a certain wavelength. The major drawback of this therapy is that the patient must remain in the dark for several days, the active substance must be modified by the addition of agents, a photosensitive one inhibiting its activity until the laser activates it, the other allowing it to be fixed on specific biological compounds in the human body. This modification therefore supposes that the active substance is fully tested pharmaceutically before it is put on the market, even if it is a known medication. Finally the doctor must have available relatively expensive equipment in the acquisition of a specific laser;

finally, there are ocular iontophoresis devices like the one indicated in patent U.S. Pat. No. 6,154,671 which describes an iontophoresis device whose reservoir comprising the active substance comes into direct contact with the eyeball. Such a device makes it possible to obtain concentrations and intra-ocular residence times equal to or greater than the techniques previously cited, whilst being non-invasive. However, the technique presented in this document remains tricky to use for long-term treatments and cannot be used when the surface of the eyeball is affected.

In the field of regional anaesthesia, outside the general anaesthesia necessary for long durations or non-cooperative patients, there are four techniques which concern the eyeball:

topical anaesthesia consists of instilling the anaesthetic topically into the conjunctival sacs. This technique gives an anaesthesia which is short but sufficient for many operations, but of poorer quality, since there is more ocular mobility, and it leads to an increase in postoperative pain. During the use of this technique, use is often made of sedatives administered intravenously and possibly leading to complications such as respiratory arrest. In this case, the presence of an anaesthetist is strongly recommended;

retrobulbar anaesthesia consists of injecting the anaesthetic using a needle at the rear of the eyeball, inside the space formed by the oculomotor muscles. This anaesthesia technique has risks of perforation of the eyeball itself, risks of retrobulbar haemorrhage, risks of injuries to the optic nerve, risks of cardiac or respiratory arrest, risks of accidental intravascular injection of the anaesthetic, and risks of retinal vascular occlusion. However, the quality and duration of the anaesthesia is good;

peribulbar anaesthesia consists of injecting the anaesthetic using a needle of the eyeball and outside the space formed by the oculomotor muscles. This technique leads to the same complications as the previous one, but less frequently, since the penetration of the needle is less deep;

finally, retrobulbar anaesthesia by catheter is a technique consisting of putting in place an epidural type catheter (between 0.4 mm and 1 mm in diameter) using a needle, within the retrobulbar or peribulbar space, so as to be able to inject the anaesthetic for operations of long duration or else to administer it continuously even postoperatively. The risks entailed by this anaesthesia technique are identical to the two previous ones.

An aim of the present invention is to provide a device for delivering ocular active substances which is very simple to use and capable of targeting the anatomical areas of the eye to be treated whilst being non-invasive.

For this there is provided, according to the invention, a device for ocular application of an active substance comprising a main electrode comprising an insulating layer and an adhesive layer able to bond the insulating layer to a conductive layer, the main electrode also having an area able to come into contact with an eyelid.

Thus, the main electrode is placed directly on the eyelid of the eye to be treated. It thus makes it possible to treat the area of the sclera which is the most permeable and which has the least risk, for vision (since there is no functional retina inside the eye around the cornea). Furthermore, the functional electrode does not come into direct contact with the eyeball. The device relies on the fact that the thickness of the skin at the eyelid is the smallest in the organism. Thus, the patient can use the device on their own without requiring the presence of a doctor, which is advantageous for iontophoreses of very long duration which have to be performed (up to 18 hours). This makes it possible to treat pathologies of the ocular adnexa and glands of the eyelids. Abnormalities of the palpebral glands are responsible for abnormalities or reduction of the quality of the tear film, and responsible for pathologies of the ocular surface.

Advantageously, the device for ocular application of an active substance has at least one of the following characteristics:
the main electrode is of oval overall shape;
the oval shape of the electrode has a large external diameter equal at most to approximately 40 mm and a small external diameter equal at most to approximately 35 mm;
the area has a non-functional central area surrounded by a functional peripheral area;
the non-functional central area is of circular shape;
the circular shape of the non-functional central area has a diameter equal at most to approximately 13 mm;
the non-functional central area is a hole passing through the electrode;
the main electrode is flexible;
the main electrode has in addition a cutaneous adhesive layer;
the main electrode has in addition a foam layer bonded to the conductive layer by a conductive adhesive layer;
the foam layer is an absorbent layer able to act as a reservoir for the active substance;
the insulating layer is a rigid casing; and the active substance is applied by iontophoresis.

There is also provided according to the invention an electrode comprising an insulating layer and an adhesive layer able to bond the insulating layer to a conductive layer, characterised in that it has a non-functional central area surrounded by a functional peripheral area able to come into contact with an eyelid.

There is also provided according to the invention a method of ocular application of an active substance comprising steps of placing a medication reservoir comprising a main electrode on the eyelids, placing a return electrode on the tissues adjacent to the eyeball to be treated, and penetration through the eyelid of the active substance under the effect of a current of energy circulating between the electrodes.

Advantageously, the method has one of the following characteristics:
prior to the placing of the active electrode on the eyelids, the active substance is disposed under the eyelids;
the main electrode has at least one of the aforementioned characteristics;
the active substance is in a topical form (liquid, suspension, gel);
the active substance is in the form of an insert.

Figure 2:
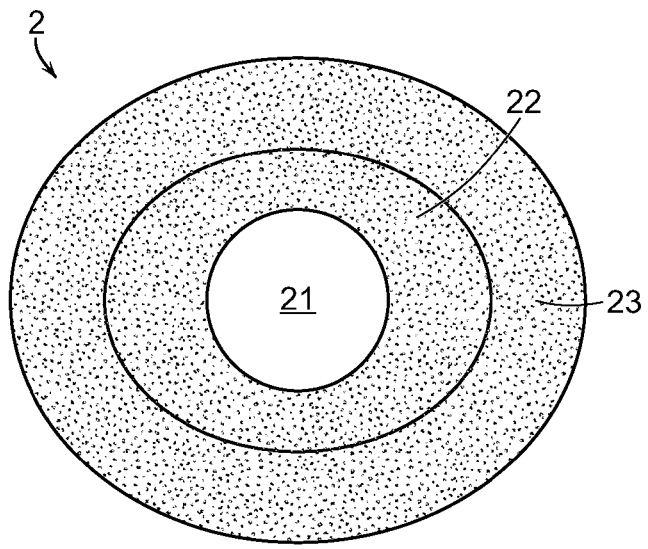
Figure 3:
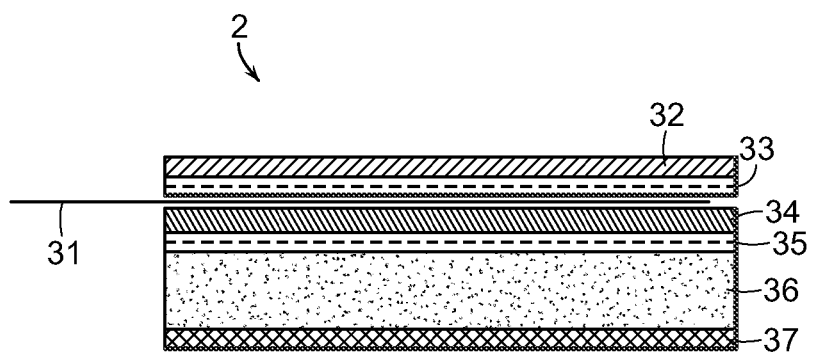
Figure 6B:
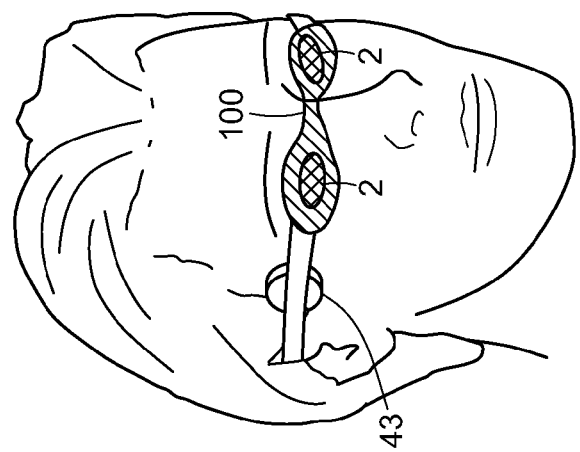
Figure 7:
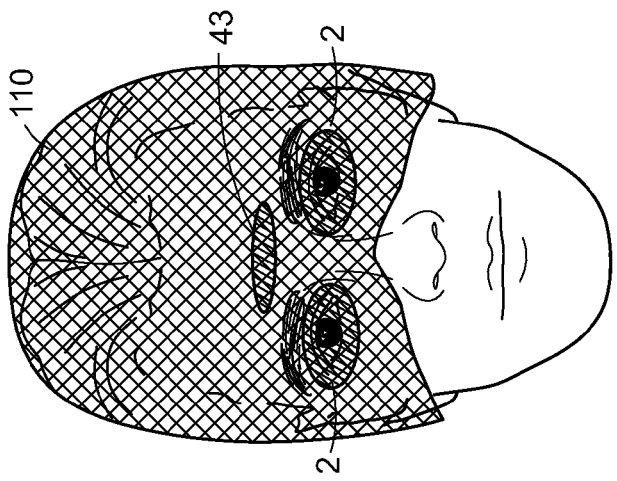
Figure 6A:
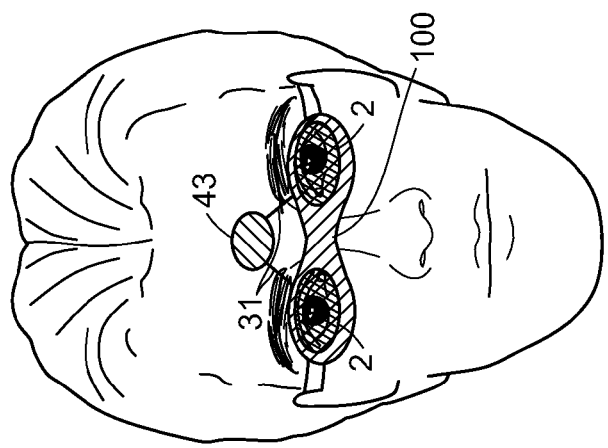
Figure 6C:
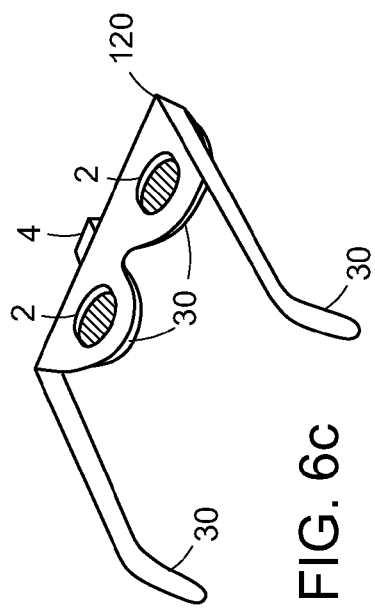

Other characteristics and advantages of the invention will emerge from the description of one embodiment and variants. In the accompanying drawings:
FIG. 1 is a schematic depiction of a device for application of an ocular active substance according to the invention;
FIG. 2 is a depiction in top view of a main electrode according to the invention;
FIG. 3 is a schematic depiction in section of he main electrode of FIG. 2;
FIG. 4 is a schematic depiction in section of the main electrode of FIG. 2 according to a variant implementation;
FIGS. 5a and 5b depict a first variant implementation of a device for application of an ocular active substance according to the invention;
FIGS. 6a, 6b and 6c depict a second variant implementation of a device for application of an ocular active substance according to the invention; and
FIG. 7 depicts a third variant implementation of a device for application of an ocular active substance according to the invention.

With reference to FIG. 1, a description will be given of the device for ocular application of an active substance by iontophoresis according to the invention. The device 1 comprises a current generator 4 connected on the one hand to a return electrode 3 and on the other hand to a main electrode 2.

The current generator 4 delivers a DC current between 0.5 mA and 5 mA preferably, perhaps even up to 10 mA, for a time between approximately 0.5 and approximately 30 minutes preferably, perhaps even up to approximately 18 hours. According to the electrical resistance of the tissues forming the circuit, a resistance liable to change during the iontophoresis, the voltage delivered by the generator is adapted according to Ohm's law, $U=R.I$, where U is the voltage in volts and R the total resistance of the circuit in ohms and I the chosen current in amperes. However the voltage delivered by this current generator can never exceed 80 V. The use can be envisaged of an alternating current generator so as to avoid an increase in pH under the effect of an oxidation-reduction phenomenon at the electrode, in particular in the case of lengthy treatment. The frequency range of these currents is chosen in order to allow a maximum increase in the permeability of the tissues of the active substance. In this particular case, the return electrode 3 must be of electrocardiogram type and consisting of an adhesive and an Ag/AgCl film of low impedance. Finally, the generator can use a current profile having very high voltage peaks, between 50 V and 2500 V approximately, over very short durations of the order of 0.01 to 0.1 seconds, at low current (like those described for electroporation).

It is possible to use other modes making it possible to improve the permeability of biological membranes: magnetophoresis which uses magnetic fields, radiofrequency and microwave electromagnetic energy, or ultrasound energy. Preferably, a device according to the invention uses iontophoresis or electroporation.

With reference to FIG. 2, the overall shape of the main electrode 2 is oval. Preferably, its large external diameter corresponds substantially to the large diameter of the eye socket, that is approximately 40 mm. Similarly, its small external diameter corresponds to the small diameter of the socket, that is approximately 35 mm. These dimensions correspond to the standard adult size of the socket. Other sizes and shapes can be envisaged depending on the age and morphology of the patient to be treated.

The electrode 2 has a central non-functional area 21. Preferably, this non-functional central area will be circular in shape with a diameter corresponding substantially to the diameter of the cornea, that is approximately 13 mm. Preferentially, the electrode comprises a central through hole acting as a non-functional area 21.

The functional peripheral area surrounding the central non-functional area has two sub-areas 22 and 23. The functional sub-area 22 is able to come opposite the surface of the sclera situated around the cornea. Similarly, the functional sub-area 23 is able to cover the surface of the eyelid where the oculomotor muscle attachments are situated.

This particular shape of the main electrode 2 makes it possible, during use, to cover the maximum surface area of the sclera around the cornea and the maximum surface area of the eyelid where the oculomotor muscle attachments are situated. It should be noted that the surface of the sclera situated around the cornea is the most permeable and presents the least risk for vision since there is no retina inside the eye around said cornea.

In general terms the main electrode 2 is flexible. Thus, the main electrode 2 conforms to the eyelid when it is put in place so as to assume the shape of the palpebral tissues as closely as possible and thus allow good electrical contact with the eyelid.

In another embodiment depicted in FIG. 4, the electrode 2 can be rigid. In this case, it is in the form of a casing 320 whose internal face is coated with a flexible material 360 able to absorb anatomical differences, so as to assume the shape of the palpebral tissues as closely as possible and thus allow good electrical contact.

The structure of the electrode will now be described with reference to FIG. 3. This depicts, in section, the six layers of material possibly constituting the electrode, certain of these layers being optional as will be seen. Each of these layers of material has a precise function.

The first layer 32 is an insulating layer. This is the part of the main electrode 2 which is able to be in contact with the operator. It makes it possible to insulate the rest of the electrode therefrom. This layer can be flexible and flat or else rigid and in the form of a casing.

The layer 33 is an adhesive layer which provides the function of bonding between the insulating layer 32 and a conductive layer 34 described below. Furthermore, this adhesive layer 33 makes it possible to hold on the conductive layer 34 an electric lead 31 connecting the main electrode 2 to the generator 4.

The layer 34 is a conductive layer. This layer consists of a silver film and a carbon film and has the function of distributing the electric current over the entire surface of the functional area of the main electrode 2. The silver film of this conductive layer is situated facing the adhesive layer 33. It allows good distribution of the current over the surface of the carbon film and provides an optimum electrical contact with the electric lead 31. For its part, the carbon film is disposed facing an absorbent foam layer 36 described below. This carbon layer resists oxidation in an aqueous medium under a DC electric current. The most suitable material is silver/carbon film with a thickness of 0.2 mm (Rexam conductive film, reference 2252, from Rexam Image Products).

The layer 36 is an optional layer. It is an absorbent foam layer able to be impregnated with the active substance or with a solution comprising the active substance before use. For this reason, this absorbent foam layer must be highly absorbent and comprise pores of small dimensions of the order of 100 to 500 micrometres. The most suitable material is, for example, open-cell hydrophilic polyurethane foam of low density of the order of 0.05 to 0.1 g/cm$^3$ (Hydrocrest™ from Crest Foam Ind, Capu-cell® from TMP Technologies inc., Amrel® from Rynel, Medicell™ Foam from Hydromer). This layer is optional depending on whether the active substance is placed in the foam before use or placed directly under the eyelid before the electrode is put in place on the eyelid.

This absorbent foam layer 36 is bonded to the carbon film of the conductive layer 34 by a conductive adhesive layer 35. This conductive adhesive must not be soluble in water.

Finally, the layer 37 is a cutaneous adhesive layer. This layer is optional depending on whether the main electrode is adhesive or not. The type of adhesive chosen must conduct electric current on the one hand and must allow the passage of the active substance whilst adhering as little as possible to the skin in order to be able to be removed easily after use. This cutaneous adhesive layer can be situated on the absorbent foam layer if the latter is present or else directly on the carbon film of the conductive layer 34.

One of the variant implementations consists of replacing the adhesive layer 33, conductive layer 34 and conductive adhesive layer 35 by a single conductive adhesive layer (AR-care® 8881 from Adhesive Research Inc.) which advantageously fulfils all the aforementioned functions.

The first embodiment of the main electrode 2 is a flexible electrode comprising a cutaneous adhesive layer 37, a conductive layer 34, an adhesive layer 33 and an insulating layer 32.

The second embodiment of the main electrode 2 is a flexible electrode comprising a cutaneous adhesive layer 37, an absorbent foam layer 36, a conductive adhesive layer 35, a conductive layer 34, an adhesive layer 33 and an insulating layer 32.

The third embodiment of the main electrode 2 is a rigid electrode in the form of a casing comprising a cutaneous adhesive layer 37, a foam layer 36 acting as a flexible material intended to absorb anatomical differences and assume the shape of the palpebral tissues as closely as possible during use, a conductive adhesive layer 35, a conductive layer 34, an adhesive layer 33 and a rigid insulating layer 32 forming the casing.

Finally, the fourth embodiment of the main electrode 2 is identical to the third embodiment described above, the foam layer being replaced by the absorbent foam layer 36.

A description will now be given of the use of the electrode and its device according to the invention.

Within the context of the first and third embodiments of the main electrode 2, the operator, who can be a doctor or the patient himself, disposes the active substance or a solution comprising the active substance under the eyelid of the eye to be treated, and then places the main electrode 2 on the eyelid and the return electrode 3 on the adjacent tissues of the eyeball to be treated. The electrodes are next connected to the generator and the circuit assembly is powered according to a defined current and a defined application time. Then, the electrodes are removed.

In the case of the second and fourth embodiments of the main electrode 2, the operator soaks the absorbent foam layer with the active substance or a solution comprising the active substance. Then he positions the main electrode on the eyelid of the eyeball to be treated and places the return electrode on the tissues surrounding the eyeball to be treated. Next the operator performs the same operations as described previously.

The various medications or active substances able to be administered by a device according to the invention are those requiring regular application or application over a long period. This is the case, for example, of corticosteroids or non-steroidal anti-inflammatories (dexamethazone, methylprednisolone hemisuccinate, etc.) whose administration must be continued over very long periods in cases of chronic inflammation.

There are also anti-allergens, neuroprotectors, neuromodulators, anti-glaucoma agents, antibiotics, antiangiogenic agents, neurotropic factors, and anaesthetics. Many other molecules are in the process of being developed for slowing down, perhaps even halting, the neovascularisation observed in degenerative pathologies of the retina. The molecules can be transferred by the transcleral route by iontophoresis or by vitreal injection and then iontophoresis. The iontophoresis device according to the invention makes it possible to simplify the administration of these medications as has been possible to see above.

Another indication of the device for application of an active substance according to the invention concerns local anaesthesia of the eyelid or the oculomotor muscles situated in the socket, which are six in number and which allow rotational movements of the eye. These are the internal rectus muscle, the external rectus muscle, the superior rectus muscle, the inferior rectus muscle, the superior oblique muscle and the inferior oblique muscle. To these are added the levator muscle of the eyelid and the orbicularis oculi muscle (can be of interest for aesthetic surgery, the treatment of exophthalmoses or ptoses). This indication allows immobilisation of the eyelid and/or akinesia of the eye within the context of surgical operations.

Other uses of the device for ocular application of an active substance according to the invention concern active substances not requiring a recurrent application but which cannot be administered by a device having direct corneal or scleral contact for a physiological reason such as, for example, a traumatism of the surface of the eyeball or following aftereffects of a surgical nature. Amongst the active substances determined, there can be cited antibiotics, antivirals, anti-inflammatories or antimycotics for example.

Of course, many modifications can be made to the invention without for all that departing from the scope thereof.

For example:

The return electrode 3 disposed on the tissues adjacent to the eyeball can be connected to the main electrode 2 by means of a non-conductive film 50 and disposed on the temple of the patient to be treated as illustrated in FIGS. 5a and 5b.

There can be two main electrodes 2 (one for each eye), disposed on a mask 100 (such as a sleeping mask used in air transport for example), the return electrode 3 associated with the generator (component 43) can be placed on the forehead of the patient preferentially, and connected to the main electrodes by means of electric leads 31, as illustrated in FIG. 6a. It should be noted that the mask 100 is held on the head of the patient by elastic means such as a headband.

In a variant illustrated in FIG. 6b of the arrangement described previously, a return electrode and the generator (component 43) can be placed advantageously inside the elastic headband for holding the mask 100 comprising the two main electrodes 2, so that the return electrode is on one of the temples (or else both in a variant disposition where there are two return electrodes). Here, the elastic holding means also serves as an electric lead which is implemented in the form of conductive tracks for example.

FIG. 6c illustrates a pair of spectacles 120 comprising two main electrodes 2 situated in place of the lenses of the pair of spectacles 120. A generator 4 is installed on the frame of the pair of spectacles 120 and connected, on the one hand, to the two electrodes 2 and, on the other hand, to the return electrodes 30 which are, preferably, situated beneath the main electrodes 2 so as to be in contact (whilst being insulated from these main electrodes) with the skin of the top of the cheeks of the patient or situated on the ends of the side-pieces of the pair of spectacles 120 so as to be in contact with the skin situated behind the ears of the patient.

FIG. 7 illustrates another variant implementation in which the two main electrodes 2 are mounted on a cap 110, as is the component 43 comprising the generator and the return electrode.

In the last four variants illustrated in FIGS. 6a, 6b, 6c and 7, the return electrode can be placed on the tissues of the face surrounding the eyeball such as the temples, the forehead, the cheeks, etc., in general terms. Furthermore, the generator can be associated therewith or not. It is possible, in variants, to place at a distance the generator connected to the main 2 and return 3 electrodes by means of electrical wires. In the contrary case, the connecting wires are integrated with the device in the form of conductive tracks for example.

These four embodiments are well adapted for treating degenerative pathologies such as diabetic retinopathy, macular degeneration related to age, and pigmentary retinitis. This is because it is known, for these pathologies, that the probability that both eyes are affected is high (of the order of 50% of cases). In this case, it is necessary to treat both eyes at the same time or over one and the same time interval alternately.

What is claimed is:

1. A system for ocular application of an active substance, comprising:

an insert adapted for placement thereof between an eyelid of a first eye and the eyeball of the first eye when the first eye is in a closed position, the insert comprising an active substance;

a main electrode adapted for placement on an outer surface of the eyelid of the first eye such that the electrode does not come into direct contact with the eyeball, the main electrode comprising a functional area configured to deliver current through the eyelid and the insert, and into the eyeball.

2. The system of claim 1, wherein the insert comprises a functional area and a non-functional central area, the functional area of the insert circumferentially surrounding the non-functional central area of the insert and containing the active substance.

3. The system of claim 2, wherein the functional area of the insert is configured to substantially cover a sclera of the eyeball and the non-functional central area of the insert is configured to substantially cover a cornea of the eyeball, when the insert is positioned between the eyelid of a first eye and the eyeball of the first eye.

4. The system of claim 1, wherein the main electrode includes an insulating layer and an adhesive layer able to bond the insulating layer to a conductive layer.

5. The system of claim 1, wherein the main electrode includes a contact area configured for coming into contact with the eyelid.

6. The system of claim 1, wherein the main electrode is configured to conform to the eyelid so as to assume the shape of palperbral tissues of the eyelid.

7. The system of claim 1, wherein the main electrode is configured for forming an electrical contact with the eyelid.

8. The system of claim 1, wherein the main electrode is rigid.

9. The system of claim 8, wherein the main electrode is a casing including an internal face thereof coated with a flexible material configured for enabling the main electrode to assume a shape of palpebral tissues of the eyelid.

10. The system of claim 1, wherein the main electrode includes a central non-functional area.

11. The system of claim 10, wherein the central non-functional area of the main electrode is circular in shape with a diameter corresponding substantially to the diameter of the cornea.

12. The system of claim 10, wherein the central non-functional area of the main electrode is comprised of a central through hole in the main electrode.

13. The system of claim 1, wherein the functional area of the main electrode includes a sub-area configured for positioning on the eyelid opposite a surface of a sclera of the eyeball.

14. The system of claim 1, wherein the functional area of the main electrode includes a sub-area configured for positioning on a surface of the eyelid where the oculomotor muscle attachments are situated.

15. The system of claim 1, wherein the overall shape of the main electrode is oval.

16. The system of claim 15, wherein dimensions of the oval are configured to substantially match the dimensions of an eye socket of the first eye.

17. The system of claim 1 further comprising a return electrode.

18. The system of claim 17, wherein the return electrode is adapted for placement on a tissue surface proximal to the first eye.

19. The system of claim 17 further comprising a current generator for generating a current between the main electrode and the return electrode including the current that flows through the eyelid and the insert, and into the eyeball.

20. The system of claim 1, wherein the main electrode is an active electrode.

* * * * *